United States Patent
Levenson et al.

(10) Patent No.: US 10,307,542 B2
(45) Date of Patent: Jun. 4, 2019

(54) HANDLE FOR A MEDICINAL PEN

(71) Applicant: David I. Levenson, Boca Raton, FL (US)

(72) Inventors: David I. Levenson, Boca Raton, FL (US); Larry E. Levenson, Boca Raton, FL (US); Arie O. Holtz, Jerusalem (IL)

(73) Assignee: David I. Levenson, Boca Raton, FL (US)

( * ) Notice: Subject to any disclaimer, the term of this patent is extended or adjusted under 35 U.S.C. 154(b) by 386 days.

(21) Appl. No.: 15/160,735

(22) Filed: May 20, 2016

(65) Prior Publication Data

US 2017/0333636 A1    Nov. 23, 2017

(51) Int. Cl.
*A61M 5/315* (2006.01)
*A61M 5/31* (2006.01)

(52) U.S. Cl.
CPC ...... *A61M 5/31553* (2013.01); *A61M 5/3137* (2013.01); *A61M 5/31551* (2013.01); *A61M 2005/3139* (2013.01); *A61M 2205/586* (2013.01); *A61M 2207/00* (2013.01)

(58) Field of Classification Search
CPC ............ A61M 5/3137; A61M 5/31551; A61M 5/31553; A61M 2005/3139; A61M 5/31525; A61M 5/31541
See application file for complete search history.

(56) References Cited

U.S. PATENT DOCUMENTS

| 4,184,490 A | 1/1980 | Jacklich |
| 4,498,904 A | 2/1985 | Turner et al. |
| 5,207,646 A | 5/1993 | Brunel |
| 5,480,387 A * | 1/1996 | Gabriel ............ A61M 5/20 604/134 |
| 5,935,100 A * | 8/1999 | Myers ............ F16K 7/17 251/61 |
| 5,957,314 A | 9/1999 | Nishida et al. |
| 6,074,372 A * | 6/2000 | Hansen ............ A61M 5/31525 604/211 |
| 6,454,746 B1 | 9/2002 | Bydlon et al. |
| 6,524,280 B2 * | 2/2003 | Hansen ............ A61M 5/31525 604/207 |
| 6,692,472 B2 * | 2/2004 | Hansen ............ A61M 5/20 604/210 |
| 6,945,961 B2 * | 9/2005 | Miller ............ A61M 5/31525 604/207 |

(Continued)

FOREIGN PATENT DOCUMENTS

| WO | 2015/074984 A1 | 5/2015 | |
| WO | WO-2016091840 A1 * | 6/2016 | ........ A61M 5/2033 |

OTHER PUBLICATIONS

International Search Report dated Aug. 4, 2017 in connection with PCT/US2017/033269.

(Continued)

*Primary Examiner* — Imani N Hayman
*Assistant Examiner* — Tiffany Legette
(74) *Attorney, Agent, or Firm* — Akerman LLP (57) ABSTRACT

According to one embodiment, a handle includes a frame and a connection surface coupled to the frame. The connection surface is configured to grasp a rotary dial of a medicinal pen. The handle further includes a cap rotatingly coupled to the frame. The cap is configured to rotate with respect to the frame.

7 Claims, 8 Drawing Sheets

(56) References Cited

U.S. PATENT DOCUMENTS

| | | | | |
|---|---|---|---|---|
| 2003/0097096 A1* | 5/2003 | Niedospial, Jr. | ..... | A61M 5/3129 604/218 |
| 2013/0079786 A1* | 3/2013 | Bonnin | .............. | A61B 17/8827 606/94 |
| 2013/0317452 A1* | 11/2013 | Heald | ............... | A61M 5/31545 604/246 |
| 2014/0066862 A1* | 3/2014 | Schweers | ............ | A61M 5/3129 604/227 |

OTHER PUBLICATIONS

Written Opinion dated Aug. 4, 2017 in connection with PCT/US2017/033269.

Youtube, "Insulin pens with large dial video," 4 pages, uploaded Dec. 13, 2009, 4 pages. https://www.youtube.com/watch?v=snKu5Kb8yic.

* cited by examiner

FIG. 7

HANDLE FOR A MEDICINAL PEN

TECHNICAL FIELD

This disclosure relates generally to the field of medicine and more specifically to a handle for a medicinal pen.

BACKGROUND

Traditionally, a person has used a medicinal pen to inject medicine (such as insulin) into their body. To do so, traditional medicinal pens include a rotary dial that the person may rotate to select an amount of medicine to inject into their body. Furthermore, this rotary dial may be depressed (or otherwise pushed down on) to inject the medicine into the person's body. Such traditional medicinal pens, however, may be deficient.

SUMMARY

According to one embodiment, a handle includes a frame and a connection surface coupled to the frame. The connection surface is configured to grasp a rotary dial of a medicinal pen. The handle further includes a cap rotatingly coupled to the frame. The cap is configured to rotate with respect to the frame.

Certain embodiments of the disclosure may provide one or more technical advantages. For example, the connection surface of the handle may grasp a rotary dial of the medicinal pen. As such, the handle may be inserted onto (and/or over) the rotary dial of the medicinal pen, and the frame may be used to rotate the rotary dial of the medicinal pen. In such an example, the larger diameter of the frame (in comparison to the smaller diameter of the rotary dial) may make rotating the rotary dial easier, for example. As another example, the size and/or shape of an opening of the connection surface (and/or the material that the connection surface is made of) may allow the handle to be inserted onto the rotary dial of many different types of medicinal pens. In such an example, a person may be able to use the handle with any type of medicinal pen, as opposed to only being able to use it with one type of medicinal pen. As a further example, when the handle is inserted onto the rotary dial, the cap may be used to depress the rotary dial in order to inject the medicine. In such an example, the larger diameter of the cap (in comparison to the smaller diameter of the rotary dial) may make depressing the rotary dial easier, for example, by increasing the surface area available for depression. This may allow a user to use several fingers (or even their palm) to depress the rotary dial, as opposed to just one finger as current medicinal pens may require. As another example, the cap may rotate with respect to the frame and the connection surface. In such an example, a person may be able to more easily use the handle with a medicinal pen that has a rotary dial that rotates when depressed.

Certain embodiments of the disclosure may include none, some, or all of the above technical advantages. One or more other technical advantages may be readily apparent to one skilled in the art from the figures, descriptions, and claims included herein.

BRIEF DESCRIPTION OF THE FIGURES

For a more complete understanding of the present disclosure and its features and advantages, reference is now made to the following description, taken in conjunction with the accompanying drawings, in which.

DETAILED DESCRIPTION

Embodiments of the present disclosure are best understood by referring to FIGS. 1-6 of the drawings, like numerals being used for like and corresponding parts of the various drawings.

As is discussed above, traditional medicinal pens may be deficient. For example, some people may have difficulty rotating and/or depressing the rotary dial due to, for example, arthritis, tremors, hand deformities, difficulty in the articulation of their hands or fingers, other ailments, and/or due to having smaller (or less strong) hands or fingers (e.g., children may have smaller or less strong hands or fingers). To assist such people, some medicinal pen manufacturers may manufacture a cap that may be attached to the rotary dial. Unfortunately, such a cap may only work with a particular medicinal pen. Therefore, when a person has two different medicinal pens, the cap may only work on one of the medicinal pens because the rotary dial of each medicinal pen may have a different shape, size, and/or manner of functioning. Contrary to such typical deficiencies, the handle 22 of FIGS. 1A-5 may provide one or more advantages, as are discussed below.

Figures 1A, 1B:
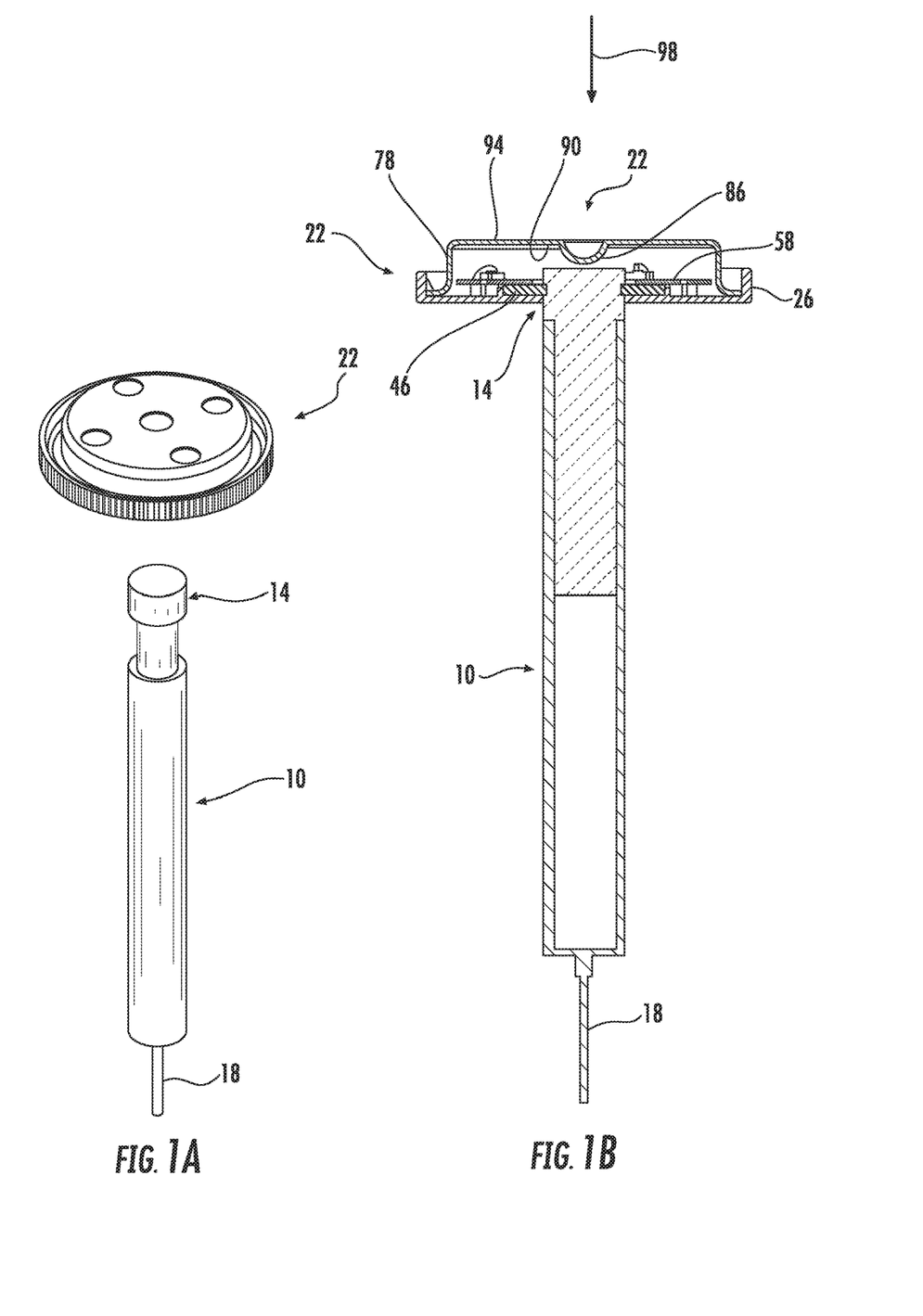
FIGS. 1A-1C illustrate an example handle that may be used with a medicinal pen.
Figure 1C:
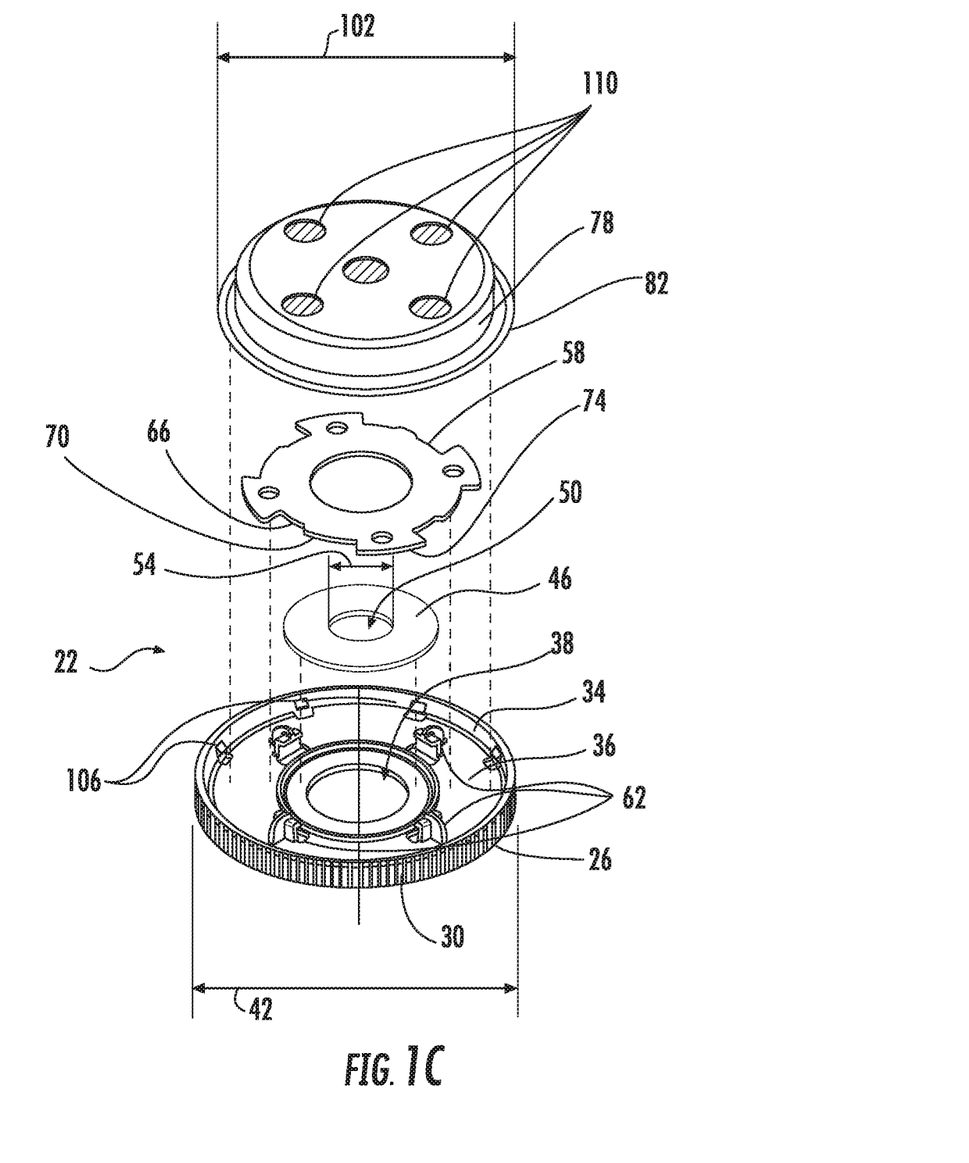

FIGS. 1A-1C illustrate an example handle 22 that may be used with a medicinal pen 10. In particular, FIG. 1A illustrates a perspective view of an example handle 22 positioned above a medicinal pen 10; FIG. 1B illustrates a cross-sectional view of a rotary dial 14 of a medicinal pen 10 inserted into an example handle 22; and FIG. 1C illustrates an exploded perspective view of an example handle 22.

As illustrated, the handle 22 includes a frame 26, a connection surface 46 coupled to the frame 26, and a cap 78 rotatingly coupled to the frame 26. The connection surface 46 may grasp a rotary dial 14 of the medicinal pen 10. For example, the connection surface 46 may include an opening 50 that may receive the rotary dial 14 of the medicinal pen 10, and that may be sized to grasp and hold the rotary dial 14. As such, the handle 22 may be inserted onto the rotary dial 14 of the medicinal pen 10, and the frame 26 may be used to rotate the rotary dial 14 of the medicinal pen 10. In such an example, the larger diameter of the frame 26 (in comparison to the smaller diameter of the rotary dial 14) may make rotating the rotary dial 14 easier, for example. Additionally, the size and/or shape of the opening 50 of the connection surface 46 (and/or the material that the connection surface 46 is made of) may allow the handle 22 to be inserted onto the rotary dial 14 of many different types of medicinal pens 10. In such an example, a person may be able to use the handle 22 with any type of medicinal pen 10, as opposed to only being able to use it with one type of medicinal pen 10. Furthermore, when the handle 22 is inserted onto the rotary dial 14, the cap 78 may be used to depress the rotary dial 14 in order to inject the medicine. In such an example, the larger diameter of the cap 78 (in comparison to the smaller diameter of the rotary dial 14) may make depressing the rotary dial 14 easier, for example, by increasing the surface area available for depression. This may allow a user to use several fingers (or even their palm) to depress the rotary dial 14, as opposed to just one finger as current medicinal pens may require. As another example, the cap may rotate with respect to the frame and the connection surface. In such an example, a person may be able to more easily use the handle with a medicinal pen that has a rotary dial that rotates when depressed.

The medicinal pen 10 may be any pen-like instrument that may be used to inject medicine (or any other pharmaceutical or nutraceutical product) into a body. For example, the medicinal pen 10 may be an insulin pen used to inject insulin into a body, a pain killer pen used to inject a pain killer (such as morphine) into a body, an epinephrine pen used to inject epinephrine into a body, a growth hormone pen used to inject a growth hormone into a body, any other pen-like instrument that may be used to inject any other type of medicine (or any other pharmaceutical or nutraceutical product) into a body, or any combination of the preceding. As is illustrated, the medicinal pen 10 is an insulin pen used to inject insulin into a body. Example insulin pens include the Novo Nordisk Flextouch, the Novo Nordisk Flex pen, the Sanofi-Aventis Solostar, and the Lilly Kwikpen. The medicinal pen 10 may be used to inject insulin (or any other medicine or pharmaceutical or nutraceutical product) into any type of body, such as the body of a person, an animal, or any other type of body. The medicinal pen 10 may be also used to inject insulin (or any other medicine or pharmaceutical or nutraceutical product) into any portion of a body, such as a leg, an arm, a shoulder, or any other portion of a body.

The medicinal pen 10 includes a rotary dial 14 and an injection port 18. The rotary dial 14 may be any device that may be rotated in order to select an amount of medicine to be injected using the medicinal pen 10. For example, the rotary dial 14 may be a dial, a button, a lever, any other device that may be rotated in order to select an amount of medicine to be injected using the medicinal pen 10, or any combination of the preceding. The rotary dial 14 may be rotated in order to select an amount of units of medicine to be injected using the medicinal pen 10. In such an example, the further the rotary dial 14 is rotated, the more units of medicine are selected (e.g., rotating the rotary dial 14 two clicks clockwise selects two units of medicine, while rotating the rotary dial 14 three clicks clockwise selects three units of medicine). The rotary dial 14 may be rotated in any direction in order to select an amount of units of medicine to be injected. For example, the rotary dial 14 may be rotated clockwise to increase the amount of medicine to be injected and counter-clockwise to decrease the amount of medicine to be injected.

The rotary dial 14 may further be depressed (or otherwise pushed down on) in order to cause the medicine to be injected. The rotary dial 14 may be depressed in any manner. For example, a person may use a finger (such as a thumb) to apply force on the rotary dial 14. The depression of the rotary dial 14 may be the result of a downward force. As another example, depending on the orientation of the medicinal pen 10, the depression of the rotary dial 14 may be the result of an upward force, a sideways force, or any other force that may cause the rotary dial 14 to be depressed (or otherwise pushed down on). To inject the medicine, the rotary dial 14 may be connected to, for example, a plunger that may inject the medicine (such an insulin) out of the medicinal pen 10 and into the body through the injection port 18.

The rotary dial 14 may have any shape. For example, the rotary dial 14 may have an outer boundary shaped as a circle, an octagon, a square, a rectangle, a triangle, an oval, a pentagon, a hexagon, a cylinder, a stadium, an irregular shape, any other shape, or any combination of the preceding. As illustrated, the rotary dial 14 is shaped as a circle. The shape of the rotary dial 14 may further include one or more indentations or protrusions that may assist a person in gripping the rotary dial 14. The rotary dial 14 may also have any size. For example, the rotary dial 14 may have an outer diameter of 12 millimeters (mm), 14 mm, 16 mm, 18 mm, or any other size. The rotary dial 14 may further be positioned at any location on the medicinal pen 10. For example, the rotary dial 14 may be positioned on the top of the medicinal pen 10, a side portion of the medicinal pen 10, or any other location on the medicinal pen 10. As illustrated, the rotary dial 14 is positioned on the top of the medicinal pen 10. Additionally, contrary to the many different sizes, shapes, and/or positions of the rotary dials 14 of medicinal pens 10, the handle 22 may be used with each of the medicinal pens 10, for example.

The rotary dial 14 may function in any manner to allow the user to select an amount of medicine to inject into their body, and may further function in any manner to allow the user to inject that amount of medicine. Furthermore, different medicinal pens 10 may have rotary dials 14 that function in different ways. For example, the Sanofi-Aventis Solostar medicinal pen 10 may include a rotary dial 14 that moves upward (or distally) in relation to the injection needle when the rotary dial 14 is rotated to select an amount of medicine. Furthermore, when the rotary dial 14 of this medicinal pen 10 is depressed (or otherwise pushed down on) to inject the medicine, the rotary dial 14 may both rotate (in the opposite direction used to select an amount of medicine) and move downward (or proximal) in relation to the injection needle. As another example, the Novo Nordisk Flextouch medicinal pen 10 may include a rotary dial 14 that is rotated to select an amount of medicine, but does not rotate when the rotary dial 14 is depressed (or otherwise pushed down on) to inject the medicine (unlike the Sanofi-Aventis Solostar medicinal pen 10 discussed above). Contrary to the many different manners in which the rotary dial 14 of the medicinal pens 10 function, the handle 22 may be used with each of the medicinal pens 10, for example.

The medicinal pen 10 further includes an injection port 18. The injection port 18 may be any port-like device for injecting medicine into a body. For example, the injection port 18 may be a needle, a needleless injection port, a nozzle, tubing, any other port-like device for injecting medicine into a body, or any combination of the preceding. The injection port 18 may have any size and/or shape. Furthermore, the injection port 18 may be positioned at any location on the medicinal pen 10.

FIGS. 1A-1C further illustrate a handle 22 that may be used with the medicinal pen 10. For example, the handle 22 may be inserted onto the rotary dial 14 of the medicinal pen 10, allowing the handle 22 to be used to assist a user in rotating the rotary dial 14 (e.g., to select an amount of medicine) and to further assist the user in depressing the rotary dial 14 (e.g., to inject the amount of medicine).

As illustrated, the handle 22 includes a frame 26, a connection surface 46 coupled to the frame 26, and a cap 78 rotatingly coupled to the frame 26. The frame 26 may be any structure that may be used to rotate the rotary dial 14 of the medicinal pen 10. For example, the frame 26 may be a base structure that may be coupled to the rotary dial 14 (as is discussed below), and that may have a diameter or surface area greater than the diameter or surface area of the rotary dial 14. As such, due to the increased diameter or surface area, a user may be able to more easily grasp the frame 26 (in comparison to the rotary dial 14) and rotate the frame 26 (to rotate the rotary dial 14).

The frame 26 may have any shape. For example, the frame 26 may have an outer boundary shaped as a circle, an octagon, a square, a rectangle, a triangle, an oval, a pentagon, a hexagon, a cylinder, a stadium, an irregular shape, any other shape, or any combination of the preceding. As illustrated, the frame 26 has an outer boundary shaped as a circle. The shape of the frame 26 may further include one or more protrusions 30 that may extend from the shape of the frame 26. The protrusions 30 may assist a user in grasping the frame 26. For example, the protrusions 30 may create ridges that may increase the frictional forces of the outer boundary of the frame 26. These ridges may make the outer boundary of the frame 26 less slippery (and therefore easier to grasp).

The shape of the frame 26 may further include a lip 34 (shown in FIG. 1C) that extends upward from a bottom portion 36 of the frame 26. The lip 34 may define the outer boundary of the frame 26. Furthermore, the lip 34 may further define a containment area that may allow one or more features (such as the connection surface 46 and a cap 78) to be coupled to the frame 26. The frame 26 may also include an opening 38 (shown in FIG. 1C). The opening 38 may be any opening (or hole) that may allow the frame 26 to be inserted onto (or coupled to) the rotary dial 14 of a medicinal pen 10. As is illustrated in FIG. 1B, the rotary dial 14 may be inserted through the opening 38 so as to extend above the bottom portion 36 of the frame 26. The opening 38 may have any shape and/or size that may allow the handle 10 to receive the rotary dial 14 through the opening 38. As is illustrated, the opening 38 is shaped as a circle. The opening 38 may have a diameter that is greater than the outer diameter of the rotary dial 14, thereby allowing the rotary dial 14 to fit within the diameter of the opening 38. Additionally, the components of the handle 10 (including, for example, the frame 26, the connection surface 46, the locking surface 58, and the cap 78), when assembled, may create a cylindrical cavity inside of the handle 10 that may receive the rotary dial 14, or a portion thereof, when the rotary dial 14 is inserted into the handle 10.

The frame 26 may be any size that may assist a user in rotating a rotary dial 14 of the medicinal pen 10. For example, the frame 26 may have an outer diameter 42 that is larger than an outer diameter of the rotary dial 14 of the medicinal pen 10. This larger outer diameter 42 of the frame 26 may allow the user (such as a user with arthritis) to more easily grasp the outer circumference (or boundary) of the frame 26 (in comparison to the smaller outer circumference of rotary dial 14).

The outer diameter 42 of the frame 26 may be any size larger than an outer diameter of the rotary dial 14. For example, if the outer diameter of the rotary dial 14 is 16 mm, the outer diameter 42 of the frame 26 may be any size greater than 16 mm. Example sizes of the outer diameter 42 of the frame 26 may include 40 mm, 45 mm, 50 mm, 55 mm, 60 mm, 65 mm, 70 mm, 75 mm, 80 mm, approximately (i.e., +/−5 mm) 40 mm, approximately 45 mm, approximately 50 mm, approximately 55 mm, approximately 60 mm, approximately 65 mm, approximately 70 mm, approximately 75 mm, approximately 80 mm, or any other size that may assist a user in rotating the rotary dial 14 of the medicinal pen 10. As another example, the size of the outer diameter 42 of the frame 26 may be within a range of 40 mm-80 mm, 50 mm-80 mm, 50 mm-70 mm, 50 mm-65 mm, 60 mm-65 mm, or any other range that may assist a user in rotating the rotary dial 14 of the medicinal pen 10. As a further example, the size of the outer diameter 42 of the frame 26 may be larger than or equal to 2 times the size of the outer diameter of the rotary dial 14, 3 times the size of the outer diameter of the rotary dial 14, 4 times the size of the outer diameter of the rotary dial 14, 5 times the size of the outer diameter of the rotary dial 14, 6 times the size of the outer diameter of the rotary dial 14, or any other amount larger than the size of the outer diameter of the rotary dial 14.

As another example, the size of the outer diameter 42 of the frame 26 may be different depending on the type of user the handle 22 is intended to be used by. For example, the size of the outer diameter 42 of the frame 26 may be different depending on whether the user is an adult person or a child, or whether the user is male or female. In such an example, the outer diameter 42 of the frame 26 may be larger if it is intended to be used by an adult, and smaller if it is intended to be used by a child.

As a result of having a larger outer diameter 42, the frame 26 may also have a larger surface area than the surface area of the rotary dial 14. For example, the frame 26 may have a surface area that larger than or equal to 3 times the size of the surface area of the rotary dial 14, 4 times the size of the surface area of the rotary dial 14, 6 times the size of the surface area of the rotary dial 14, 10 times the size of the surface area of the rotary dial 14, 15 times the size of the surface area of the rotary dial 14, 20 times the size of the surface area of the rotary dial 14, or any other amount larger than the size of the surface area of the rotary dial 14.

The frame 26 may be made of (or otherwise constructed of) any material that may allow a user to rotate the rotary dial 14 of the medicinal pen 10. For example, the frame 26 may be made of a metal (such as steel or aluminum), a rigid rubber or elastomer, a plastic or polymer (such as acrylonitrile butadiene styrene (ABS), acetyl, polypropylene, polycarbonate, polyethylene terephthalate (PET)), any other material that may allow a user to rotate the rotary dial 14 of the medicinal pen 10, or any combination of the preceding. As is illustrated, the frame 26 is made of polypropylene.

As illustrated, the handle 22 further includes a connection surface 46 coupled to the frame 26. The connection surface 46 may grasp the rotary dial 14 of the medicinal pen 10. Such a grasping of the rotary dial 14 may refer to the connection surface 46 being able to hold the rotary dial 14, so that when the connection surface 46 is rotated (with the frame 26), the hold causes the rotary dial 14 to also rotate. Such a grasp may cause the rotary dial 14 to rotate the same amount of rotation as the connection surface 46 (and frame 26). Alternatively, such a grasp may cause the rotary dial 14 to rotate a slightly less amount of rotation than the connection surface 46 and frame 26 (e.g., each 360° turn of the connection surface 46 and frame 26 causes a 350° turn of the rotary dial 14), or to rotate a slightly more amount of rotation than the connection surface 46 and frame 26 (e.g., each 360° turn of the connection surface 46 and frame 26 causes a 370° turn of the rotary dial 14). In addition to grasping the rotary dial 14 of the medicinal pen 10, the connection surface 46 may further be removable from the rotary dial 14 of the medicinal pen 10. As such, the connection surface 46 (and the handle 22) may be removed from the rotary dial 14, and the connection surface 46 may be used to grasp a different rotary dial 14 of a different medicinal pen 10. Therefore, the handle 22 may be more easily used with different medicinal pens 10 and/or may be more easily added to and removed from the same medicinal pen 10 (e.g., it may be reusable with the same or different medicinal pens 10).

The connection surface 46 may be any structure that may grasp the rotary dial of the medicinal pen 10. For example, the connection surface 46 may be a washer, a solid disc with a cutout portion for grasping the rotary dial 14, a ring, a clamping (or clasping) device for grasping the rotary dial 14, any other structure that may grasp the rotary dial 14 of the medicinal pen 10, or any combination of the preceding. As illustrated, the connection surface 46 is a washer (such as an elastomer washer) that may grasp the rotary dial 14 of the medicinal pen 10.

The connection surface 46 may grasp the rotary dial 14 in any manner. For example, the connection surface 46 may have two or more clamping (or clasping) arms that may be closed against the outer boundary of the rotary dial 14. This closure of the clamping arms may apply pressure to the rotary dial 14, and result in the rotary dial 14 being grasped by the connection surface 46. As a further example, the connection surface 46 may have one or more protrusions that may be inserted into an opening in the rotary dial 14 (e.g., where the protrusions being inserted into an opening in the rotary dial 14 is similar to a key being inserted into a respective lock). As another example, and as is illustrated in FIGS. 1A-1C, the connection surface 46 may include an opening 50 (shown in FIG. 1C) that is sized and/or shaped to grasp the rotary dial 14. In such an example, the rotary dial 14 may be inserted into the opening 50, causing the opening 50 to provide a friction-based hold (and/or a pressure-based hold) of the rotary dial 14. Therefore, as the frame 26 and the connection surface 46 is rotated, the hold on the rotary dial 14 may cause the rotary dial 14 to also rotate.

The opening 50 may have any size for grasping the rotary dial 14. For example, the opening 50 may have an inner diameter 54 that is smaller than the outer diameter of the rotary dial 14. Such a smaller inner diameter 54 may cause the connection surface 46 to apply pressure and/or friction to the outer boundary of the rotary dial 14 when the rotary dial 14 is inserted into the opening 50, thereby grasping the rotary dial 14. Furthermore, in addition to being sized to grasp the rotary dial 14, the inner diameter 54 of the opening 50 may further be sized so that the connection surface 46 (and the handle 22) may be easily removed from the rotary dial 14 (but not too easily removed, as that may cause the connection surface 46 to accidentally fall off of the rotary dial 14).

The inner diameter 54 of the opening 50 may be smaller than the outer diameter of the rotary dial 14 by any amount that allows the connection surface 46 to grasp the rotary dial 14, and that further allows the connection surface 46 to be easily removed from the rotary dial 14. As an example, the inner diameter 54 may be 0.5 mm smaller than the outer diameter of the rotary dial 14, 1 mm smaller than the outer diameter of the rotary dial 14, 1.5 mm smaller than the outer diameter of the rotary dial 14, 2.0 mm smaller than the outer diameter of the rotary dial 14, approximately (i.e., +/−0.5 mm) 0.5 mm smaller than the outer diameter of the rotary dial 14, approximately 1.0 mm smaller than the outer diameter of the rotary dial 14, approximately 1.5 mm smaller than the outer diameter of the rotary dial 14, approximately 2.0 mm smaller than the outer diameter of the rotary dial 14, or any other size smaller than the outer diameter of the rotary dial 14.

Example sizes of the inner diameter 54 of the opening 50 may include 12 mm, 13 mm, 14 mm, 15 mm, 16 mm, 17 mm, 18 mm, 20 mm, approximately (i.e., +/−1 mm) 12 mm, approximately 13 mm, approximately 14 mm, approximately 15 mm, approximately 16 mm, approximately 17 mm, approximately 18 mm, approximately 20 mm, or any other size that may allow the connection surface 46 to grasp the rotary dial 14. As another example, the inner diameter 54 of the opening 50 may be within a range of 12 mm-20 mm, 14 mm-18 mm, 14 mm-17 mm, or any other range that may allow the connection surface 46 to grasp the rotary dial 14.

The opening 50 may have any shape for grasping the rotary dial 14. For example, the opening 50 may be shaped as a circle, an octagon, a square, a triangle, an oval, a pentagon, a hexagon, an irregular shape, any other shape, or any combination of the preceding. As illustrated, the opening 50 is shaped as a circle.

The connection surface 46 may have any shape. For example, the connection surface 46 may have an outer boundary that is shaped as a circle, an octagon, a square, a triangle, an oval, a pentagon, a hexagon, an irregular shape, any other shape, or any combination of the preceding. As illustrated, the connection surface 46 has an outer boundary that is shaped as a circle. Furthermore, the connection surface 46 may have an opening 50, as is discussed above.

The connection surface 46 may further have any size. For example, the connection surface 46 may have an outer diameter that is 20 mm, 28 mm, 30 mm, 35 mm, 40 mm, 60 mm, approximately (i.e., +/−5 mm) 20 mm, approximately 28 mm, approximately 30 mm, approximately 35 mm, approximately 40 mm, approximately 60 mm, within a range of 20 mm 60 mm, within a range of 20 mm-40 mm, within a range of 28 mm-60 mm, within a range of 30 mm-40 mm, within a range of 30 mm-35 mm, or any other size. Furthermore, the connection surface 46 may have a thickness that is 1 mm, 2 mm, 2.5 mm, 3 mm, 4 mm, 5 mm, approximately (i.e., +/−0.5 mm) 1 mm, approximately 2 mm, approximately 2.5 mm, approximately 3 mm, approximately 4 mm, approximately 5 mm, within a range of 1 mm-5 mm, within a range of 1.5 mm-5 mm, within a range of 2 mm-4 mm, within a range of 2.5 mm-3 mm, or any other size.

The connection surface 46 may be coupled to the frame 26. For example, as is illustrated, the connection surface 46 may be coupled to the frame 26 so as to be coaxial with the frame 26.

The coupling of the connection surface 46 to the frame 26 may prevent the connection surface 46 from rotating with respect to the frame 26. As such, when the frame 26 is rotated, the connection surface 46 (and the rotary dial 14 being grasped by the connection surface 46) is rotated the same (or nearly the same) amount of rotation. The connection surface 46 may be coupled to the frame 26 in any manner that may prevent the connection surface 46 from rotating with respect to the frame 26. For example, the connection surface 46 may be coupled to the frame 26 by an adhesive, a locking structure 58 (as is discussed below), a welding, one or more screws, one or more nuts and bolts, one or more clips, one or more rivets, any other means of coupling that may prevent the connection surface 46 from rotating with respect to the frame 26, or any combination of the preceding. As another example, the connection surface 46 may be formed integral with the frame 26. As is illustrated, the connection surface 46 is coupled to the frame 26 by the locking surface 58.

The connection surface 46 may be coupled to any portion of the frame 26. For example, the connection surface 46 may be coupled to an inside surface of the bottom portion 36 of the frame 26, an outside surface of the bottom portion 36 of the frame 26, or any other portion of the frame 26. As is illustrated in FIGS. 1B and 1C, the connection surface 46 is coupled to the inside surface of the bottom portion of the frame 26.

The connection surface 46 may be made of (or otherwise constructed of) any material that may allow the connection surface 46 to grasp the rotary dial 14. For example, the connection surface 46 may be made of an elastomer material. This elastomer material may be flexible, so that is stretches when the rotary dial 14 is inserted into the opening 50 of the connection surface 46. As such, the elastomer material may assist the connection surface 46 in grasping the rotary dial 14, by providing a friction-based hold (and/or a pressure-based hold) of the rotary dial 14. The connection surface 46 may be made of any elastomer material, such as silicone, nitrite rubber (NBR), santoprene, styrene-butadiene rubber (SBR), any other elastomer, or any combination of the preceding. As another example, the connection surface 46 may be made of a metal (such as steel or aluminum), a plastic or polymer (such as ABS, acetyl, polypropylene, polycarbonate, PET), any other material that may allow the connection surface 46 to grasp the rotary dial 14, or any combination of the preceding. As is illustrated, the connection surface 46 is made of silicone.

As illustrated, the handle 22 further includes the locking surface 58. The locking surface 58 may be any structure that may couple the connection surface 46 to the frame 26. For example, the locking surface 58 may be a block, a locking wafer, a disc, any other structure that may couple the connection surface 46 to the frame 26, or any combination of the preceding. As illustrated, the locking surface 58 is a locking wafer. The locking surface 58 may be positioned so as to be coaxial with the connection surface 46 and frame 26, as is also illustrated.

The locking surface 58 may couple the connection surface 46 to the frame 26 in any manner. For example, the locking surface 58 may be shaped and/or sized to be locked into one or more locking hooks 62 (shown in FIG. 1C) positioned on the frame 26. In such an example, the connection surface 46 may be positioned directly on the inside surface of the bottom portion 36 of the frame 26, as is illustrated in FIG. 1C. Furthermore, the locking surface 58 may be positioned directly on top of the connection surface 46 (thereby positioning the connection surface 46 in-between a bottom portion of the locking surface 58 and an inside surface of the bottom portion of the frame 26).

In addition to being positioned directly on top of the connection surface 46, the locking surface 58 may be inserted into the locking hooks 62 on the frame 26. This insertion of the locking surface 58 into the locking hooks 62 may be accomplished by positioning the small-diameter portions 66 of the locking surface 58 in line with each of the locking hooks 62 of the frame 26. Once this positioning has occurred, the locking surface 58 may be rotated, for example, clockwise so that the medium-diameter portions 70 of the locking surface 58 are positioned underneath the hook portions of each of the locking hooks 62. Additionally, the large-diameter portions 74 of the locking surface 58 may prevent the locking surface 58 from being rotated too far clockwise, for example.

The insertion of the locking surface 58 into the locking hooks 62 may lock the locking surface 58 into the frame 26 (thereby coupling the connection surface 46 to the frame 26). Additionally, this insertion may also cause the locking surface 58 to compress the connection surface 46 in-between the frame 26 and the locking surface 58, which may further couple the connection surface 46 to the frame 26.

The locking surface 58 may have any shape and/or size for coupling the connection surface 46 to the frame 26. For example, as is discussed above, the locking surface 58 may be shaped to have small-diameter portions 66, medium-diameter portions 70, and large-diameter portions 74 to lock the locking surface 58 into the frame 26 (thereby coupling the connection surface 46 to the frame 26). Additionally, the shape of the locking surface 58 may also include an opening (or hole) that may allow the rotary dial 14 to be inserted through the opening so as to extend above the top surface of the locking surface 58. This may allow protrusions 86 (discussed below) to contact an upper surface of the rotary dial 14 of the medicinal pen 10 when a user applies force against an outside top surface 94 of the cap 78 (as is also discussed below). The opening may have any shape and/or size that may allow the rotary dial 14 to be inserted into the opening. As is illustrated, the opening in the locking surface 58 is shaped as a circle.

The locking surface 58 may be made of (or otherwise constructed of) any material that may allow the locking surface 58 to couple the connection surface 46 to the frame 26. For example, the locking surface 58 may be made of a metal (such as steel or aluminum), a rigid rubber or elastomer, a plastic or polymer (such as ABS, acetyl, polypropylene, polycarbonate, PET), any other material that may allow the locking surface 58 to couple the connection surface 46 to the frame 26, or any combination of the preceding. The locking surface 58 may be made of the same material as the frame 26 and/or the connection surface 46, or the locking surface 58 may be made of a different material. As is illustrated, the locking surface 58 is made of the same material as the frame 26, such as, for example, polypropylene.

As illustrated, the handle 22 further includes a cap 78 rotatingly coupled to the frame 26. The cap 78 may be any structure that may assist the user in depressing (or otherwise pushing down on) the rotary dial 14 of the medicinal pen 10, and that may further rotate with respect to the frame 26 (and connection surface 46). For example, the cap 78 may be a solid disc, a hollowed out disc, a cover, a plate, any other structure that may assist the user in depressing (or otherwise pushing down on) the rotary dial 14 of the medicinal pen 10, and that may further rotate with respect to the frame 26, or any combination of the preceding. As illustrated, the cap 78 is a solid disc. The cap 78 may be positioned so as to be coaxial with the locking surface 58, connection surface 46, and frame 26, as is also illustrated.

The cap 78 may have any shape. For example, the cap 78 may have an outer boundary shaped as a circle, an octagon, a square, a rectangle, a triangle, an oval, a pentagon, a hexagon, a cylinder, a stadium, an irregular shape, any other shape, or any combination of the preceding. As illustrated, the cap 78 has an outer boundary shaped as a circle. In addition to the shape of the cap 78, the cap 78 may further include a lip 82 (shown in FIG. 1C) that extends horizontally outward from the shape of the cap 78. The lip 78 may allow the cap 78 to be rotatingly coupled to the frame 26, as is discussed below.

Furthermore, the shape of the cap 78 may further include one or more protrusions 86 extending from the inside top surface 90 of the cap 78 towards the frame 26. A protrusion 86 may be any feature that may contact an upper surface of the rotary dial 14 of the medicinal pen 10 when a user applies force against an outside top surface 94 of the cap 78. An example of such a force is illustrated in FIG. 1B as downward force 98. By contacting an upper surface of the rotary dial 14 of the medicinal pen 10, the protrusion 86 may be able to focus the force applied by the user onto the top surface of the rotary dial 14 (causing the rotary dial 14 to be depressed). As such, the user may apply the force 98 on any portion of the cap 78, and may still be able to depress (or otherwise push down on) the rotary dial 14 in order to inject the medicine. The protrusion 86 may have any size and/or shape. Furthermore, the cap 78 may have any number of protrusions 86, such as 1 protrusion 86, 2 protrusions 86, 3 protrusions 86, 4 protrusions 86, or any other number of protrusions 86.

Additionally, although the protrusion 86 has been described as contacting an upper surface of the rotary dial 14 of the medicinal pen 10 when a user applies force against an outside top surface 94 of the cap 78, the protrusion 86 may further contact the upper surface of the rotary dial 14 even when a user is not applying force against the outside top surface 94 of the cap 78. For example, the protrusion 86 may be sized and/or shaped to continuously contact the upper surface of the rotary dial 14 when the rotary dial 14 is inserted into the handle 22.

A user may apply a force against the cap 78 (such as to an outside top surface 94 of the cap 78) in order to depress the rotary dial 14 of the medicinal pen 10. The force may be applied against the cap 78 in any manner. For example, a user may apply the force using one or more fingers (such as a thumb or index finger), a palm of a hand, one or more hands, a surface (such as pressing the outside top surface 94 of the cap 78 against a desk surface to inject the medicine), any other manner of applying a force, or any combination of the preceding.

The cap 78 may have any size that may assist a user in depressing the rotary dial 14 in order to inject the medicine. For example, the cap 78 may have an outer diameter 102 that is larger than an outer diameter of the rotary dial 14 of the medicinal pen 10. This larger outer diameter 102 of the cap 78 may allow the user (such as a user with arthritis) to more easily push down on (or otherwise apply force to) the rotary dial 14 (using the cap 78) by increasing the surface area available for depression, in comparison to the smaller outer diameter of the rotary dial 14. This may allow a user to use several fingers (or even their palm) to depress the rotary dial 14, if desired, using the cap 78.

The outer diameter 102 of the cap 78 may have any size larger than an outer diameter of the rotary dial 14. For example, if the outer diameter of the rotary dial 14 is 16 mm, the outer diameter 102 of the cap 78 may be any size greater than 16 mm Example sizes of the outer diameter 102 of the cap 78 may include 39 mm, 44 mm, 49 mm, 54 mm, 59 mm, 64 mm, 69 mm, 74 mm, 79 mm, approximately (i.e., +/−5 mm) 39 mm, approximately 44 mm, approximately 49 mm, approximately 54 mm, approximately 59 mm, approximately 64 mm, approximately 69 mm, approximately 74 mm, approximately 79 mm, or any other size that may assist a user in depressing the rotary dial 14 in order to inject the medicine. As another example the size of the outer diameter 102 of the cap 78 may be within a range of 39 mm-80 mm, 49 mm-80 mm, 49 mm-70 mm, 49 mm-65 mm, 59 mm-65 mm, or any other range that may assist a user in depressing the rotary dial 14 in order to inject the medicine. In a further example, the outer diameter 102 of the cap 78 may be smaller than the outer diameter 42 of the frame 26, thereby allowing the cap 78 to fit within the frame 26.

As is discussed above, the cap 78 is rotatingly coupled to the frame 26. The cap 78 may be rotatingly coupled to the frame 26 in any manner. For example, the frame 26 may include one or more mechanical tracks that may couple the cap 78 to the frame 26, and allow the cap 78 to rotate with respect to the frame 26. As another example, the frame 26 may include one or more wheels or gears that may couple the cap 78 to the frame 26, and allow the cap 78 to rotate with respect to the frame 20. As a further example, and as illustrated in FIG. IC, the frame 26 may include one or more rotational hooks 106. In such an example, the lip 82 of the cap 70 may be positioned underneath the hook portion of the rotational hooks 106. This positioning may couple the cap 78 to the frame 26, but may further allow the cap 78 to rotate with respect to the frame 26.

As a result of the cap 78 being rotatingly coupled to the frame 26 (and thereby able to rotate with respect to the frame 26 and the connection surface 46), the handle 22 may more easily work with a rotary dial 14 that rotates when depressed by a user. For example, as is discussed above, particular medicinal pens 10 (such as the Sanofi-Aventis Solostar medicinal pen 10) include a rotary dial 14 that rotates when a user depresses (or otherwise pushes down on) the rotary dial 14 in order to inject the medicine. In such an example, the handle 22 may be inserted onto such a rotary dial 14, and the cap 78 may not rotate when the rotary dial 14 rotates from being depressed. In particular, when the user presses down on the cap 78, the cap 78 may depress (or otherwise pushed down on) the rotary dial 14 of the medicinal pen 10, causing the rotary dial 14 to rotate. However, due to the rotating coupling of the cap 78 to the frame 26, the cap 78 may not rotate at all. Instead, the rotation of the rotary dial 14 may cause only the frame 26 (and the connection surface 46, which is grasping the rotary dial 14, and the locking surface 58) to rotate with the rotary dial 14 of the medicinal pen 10. This rotation of the frame 26 (and the connection surface 46 and the locking surface 58) may cause the frame 26 (and the connection surface 46 and the locking surface 58) to rotate with respect to the cap 78. It may not, however, cause the cap 78 rotate at all (or only a minor amount, due to friction). As such, the cap 78 may be easier to push down on by a user because the cap 78 may not rotate when the rotary dial 14 rotates.

The cap 78 may be made of any material that may assist the user in depressing (or otherwise pushing down on) the rotary dial 14 of the medicinal pen 10 using the cap 78, and that may further allow the cap 78 to rotate with respect to the frame 26 (and connection surface 46). For example, the cap 78 may be made of a metal (such as steel or aluminum), a rigid rubber or elastomer, a plastic or polymer (such as ABS, acetyl, polypropylene, polycarbonate, PET), any other material that may assist the user in depressing (or otherwise pushing down on) the rotary dial 14 of the medicinal pen 10 using the cap 78, and that may further allow the cap 78 to rotate with respect to the frame 26 (and connection surface 46), or any combination of the preceding. In one example, the material of the cap 78 and the material of the frame 26 may both be selected to reduce friction between the cap 78 and the frame 26 and/or may both be selected to reduce the weight of the handle 22. The cap 78 may be made of the same material as the frame 26, the connection surface 46, and/or the locking surface 58, or the cap 78 may be made of a different material. As is illustrated, the locking surface 58 is made of the same material as the frame 26 and the locking surface 58, such as, for example, polypropylene.

The cap 78 may further include one or more rubber tips 110 positioned on the outside top surface 94 of the cap 78. A rubber tip 110 may be a structure that may increase the friction between the cap 78 and another surface, such as a desk. By increasing the friction, the rubber tip 110 may allow the handle 22 to be positioned upside down on the other surface (such as a desk) without the handle 22 slipping over the surface (or reducing the amount of slippage). As such, the rotary dial 14 of the medicinal pen 10 may be more easily inserted into the handle 22. For example, some users (such as users with arthritis) may have difficulty inserting the rotary dial 14 into the handle 22. To alleviate this problem, the handle 22 may be placed upside down on a surface (such as a desk), and then the medicinal pen 10 may be turned upside down and the rotary dial 14 may be inserted into the handle 22. While doing so, the rubber tips 110 may prevent the handle 22 from slipping on the surface (or reduce the amount of slippage), which may make the insertion of the rotary dial 14 into the handle 22 easier, for example.

The cap 78 may include any number of rubber tips 110. For example, the cap 78 may include 1 rubber tip 110, 2 rubber tips 110, 3 rubber tips 110, 4 rubber tips 110, 5 rubber tips 110, or any other number of rubber tips 110. As illustrated, the cap 78 includes 4 rubber tips 110. The rubber tips 110 may have any shape. For example, the rubber tips 110 may have an outer boundary shaped as a circle, an octagon, a square, a rectangle, a triangle, an oval, a pentagon, a hexagon, a cylinder, a stadium, an irregular shape, any other shape, or any combination of the preceding. As illustrated, the rubber tips 110 are shaped as a circle.

The rubber tips 110 may be coupled to the outside top surface 94 of the cap 78. The rubber tips 110 may be coupled to the outside top surface 94 of the cap 78 in any manner. For example, the rubber tips 110 may be coupled to the outside top surface 94 of the cap 78 by an adhesive, one or more screws, one or more nuts and bolts, one or more clips, one or more rivets, any other means of coupling, or any combination of the preceding. As another example, the rubber tips 110 may be formed integral with the outside top surface 94 of the cap 78. As is illustrated, the rubber tips 110 are coupled to the outside top surface 94 of the cap 78 by an adhesive.

The rubber tips 110 may be made of (or otherwise constructed of) any material that may increase the friction between the cap 78 and another surface. For example, the rubber tips 110 may be made of an elastomer material, such silicone, NBR, santoprene, SBR, any other elastomer, or any combination of the preceding.

Modifications, additions, combinations, or omissions may be made to the handle 22 of FIGS. 1A-1C without departing from the scope of the disclosure. For example, although the cap 78 has been described above as rotating with respect to the frame 26, in some examples the cap 78 may not rotate with respect to the frame 26. As another example, although the handle 22 has been described above as including a locking surface 58, in some examples the handle 22 may not include a locking surface 58. Instead, the connection surface 46 may be coupled to the frame 26 in another manner, such as using an adhesive. As a further example, although the connection surface 46 has been described above as being separate from the frame 26, in some examples the connection surface 46 may be integral with the frame 26 or form a portion of the frame 26.

Additionally, although the handle 22 has been described above as being used with a medicinal pen 10 (such as an insulin pen), the handle 22 may be used (and sized to be used) with any other device that a user may have difficulty opening or depressing, such as soda bottles, medicine bottles, jars, or any other device that a user may have difficulty opening or depressing.

Figure 2:
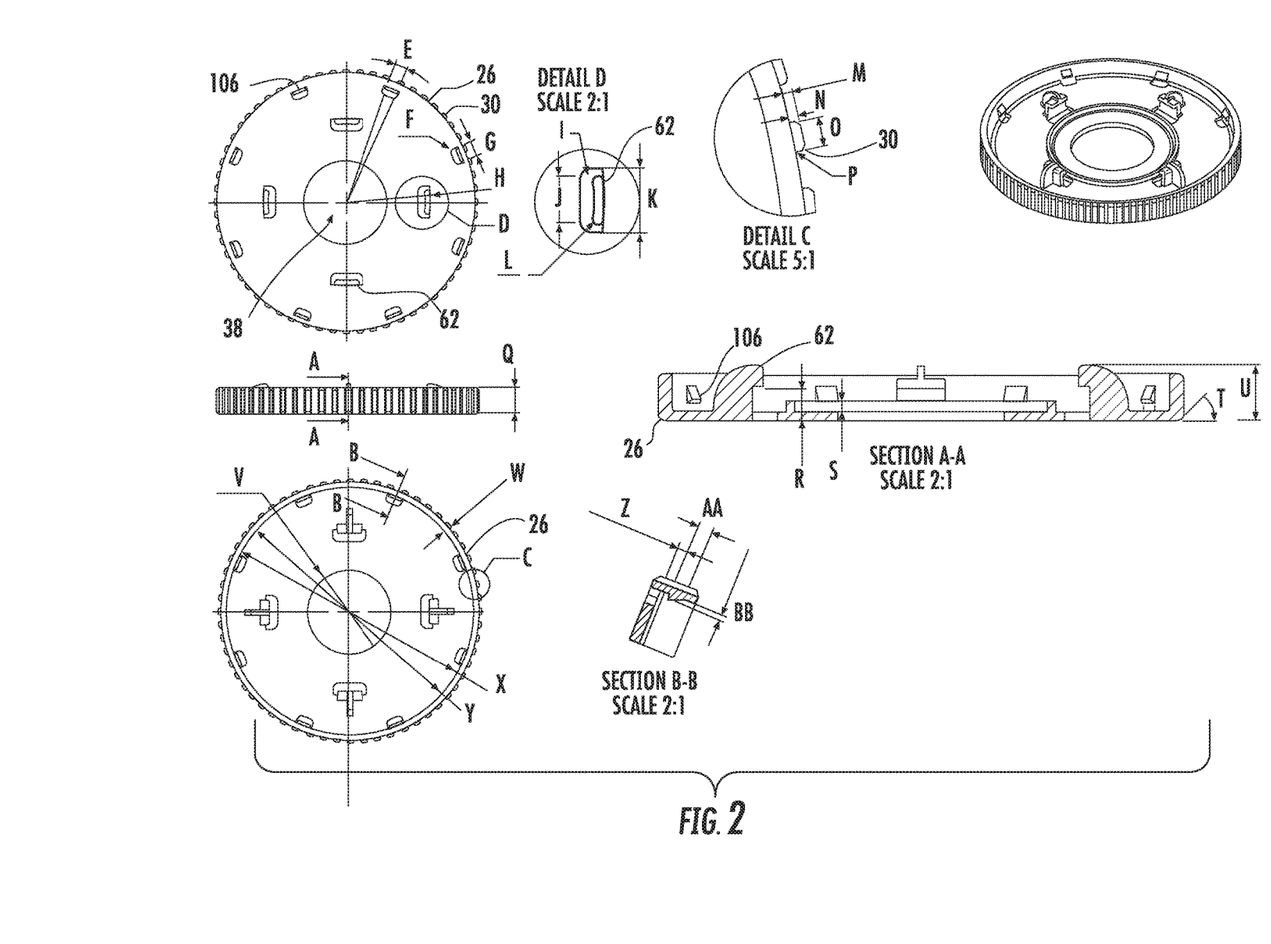
FIG. 2 illustrates various views of one example of a frame of a handle.

FIG. 2 illustrates various views of one example of a frame 26. The frame 26 of FIG. 2 may be similar to the frame 26 of FIGS. 1A-1C. Additionally, the frame 26 may have the following dimensions:
E=5 degrees+/−1 degrees
F=radius of 1 mm+/−0.1 mm
G=4 mm+/−0.1 mm
H=radius of 21.20 mm+/−0.2 mm
I=radius of 1 mm+/−0.1 mm×6
J=6 mm+/−0.1 mm
K=8 mm+/−0.2 mm
L=radius of 0.5 mm+/−0.1 mm
M=0.5 mm+/−0.1 mm
N=0.2 mm+/−0.1 mm×45 degrees
O=1.5 mm+/−0.1 mm
P=radius of 0.2 mm+/−0.1 mm
Q=6 mm+/−0.1 mm
R=3.2 mm+/−0.1 mm
S=1.40 mm+/−0.1 mm
T=45 degrees+/−1 degree
U=7.20 mm+/−0.2 mm
V=diameter of 21 mm+/−0.2 mm
W=1.2 mm+/−0.1 mm
X=diameter of 61.20 mm+/−0.3 mm
Y=diameter of 62.60 mm+/−0.3 mm
Z=1.20 mm+/−0.1 mm
AA=2 mm+/−0.1 mm
BB=0.70 mm+/−0.1 mm Although the frame 26 has been illustrated as including particular dimensions, the frame 26 may have any other dimensions.

Figure 3:
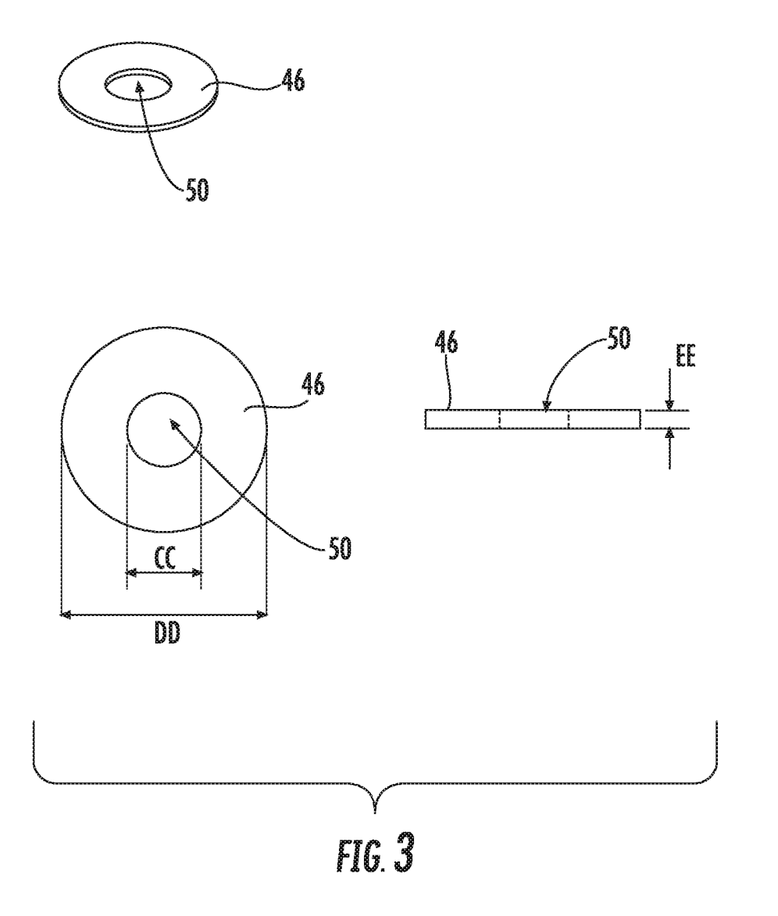
FIG. 3 illustrates various views of one example of a connection surface of a handle.

FIG. 3 illustrates various views of one example of a connection surface 46. The connection surface 46 of FIG. 3 may be similar to the connection surface 46 of FIGS. 1A-1C. Additionally, the connection surface 46 may have the following dimensions:
CC=15.0 mm+/−0.2 mm
DD=31.8 mm+/−0.3 mm
EE=2.50 mm+/−0.1 mm Although the connection surface 46 has been illustrated as including particular dimensions, the connection surface 46 may have any other dimensions.

Figure 4:
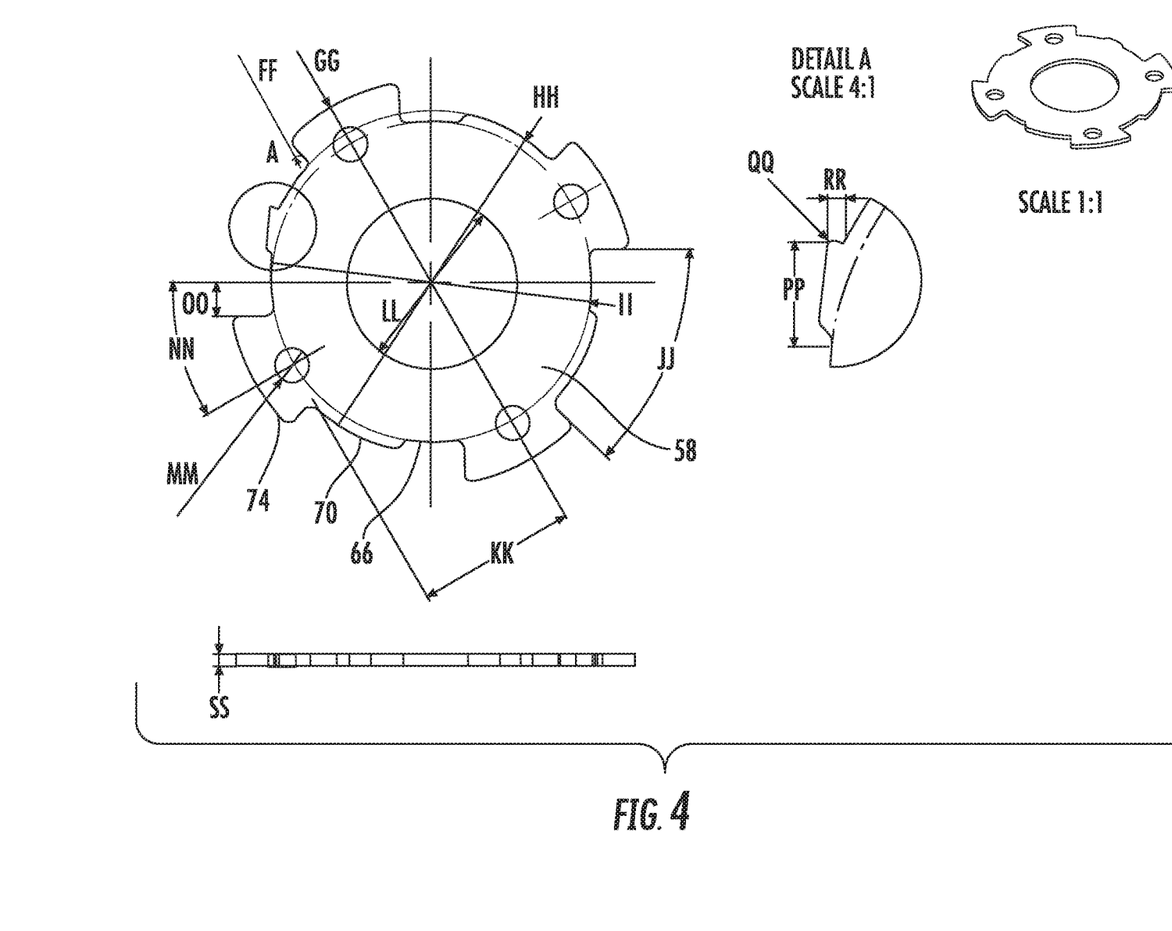
FIG. 4 illustrates various views of one example of a locking surface of a handle.

FIG. 4 illustrates various views of one example of a locking surface 58. The locking surface 58 of FIG. 4 may be similar to the locking surface 58 of FIGS. 1A-1C. Additionally, the locking surface 58 may have the following dimensions:
FF=radius of 1 mm+/−0.1 mm
GG=diameter of 50 mm+/−0.3 mm
HH=diameter of 42.20 mm+/−0.3 mm
II=diameter of 39.80 mm+/−0.3 mm
JJ=45 degrees+/−1 degree
KK=20 mm+/−0.2 mm
LL=diameter of 21 mm+/−0.2 mm
MM=diameter of 4.10 mm+/−0.1 mm
NN=30 degrees+/−1 degree
OO=4 mm+/−0.1 mm
PP=6.49 mm+/−0.2 mm
QQ=radius of 0.25 mm+/−0.1 mm
RR=1.05 mm+/−0.1 mm
SS=1.20 mm+/−0.1 mm Although the locking surface 58 has been illustrated as including particular dimensions, the locking surface 58 may have any other dimensions.

Figure 5:
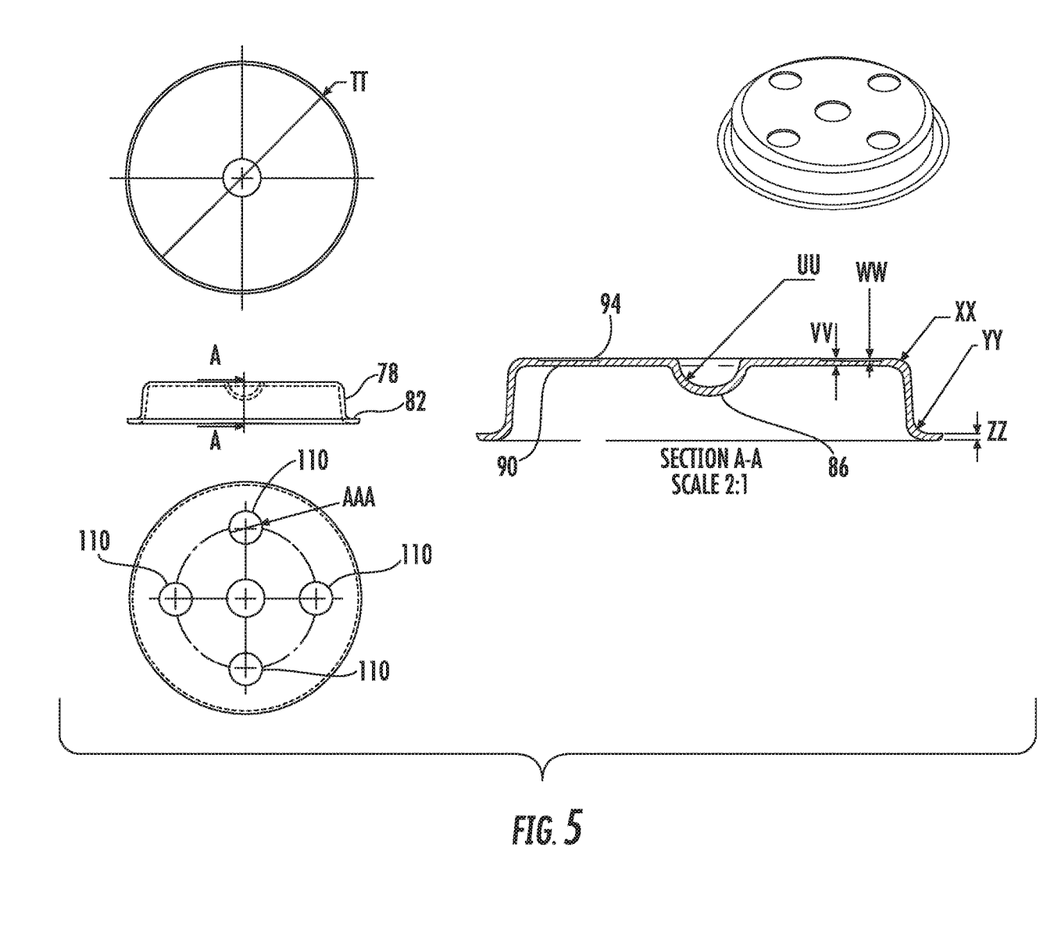
FIG. 5 illustrates various views of one example of a cap of a handle.

FIG. 5 illustrates various views of one example of a cap 78. The cap 78 of FIG. 5 may be similar to the cap 78 of FIGS. 1A-1C. Additionally, the cap 78 may have the following dimensions:
TT=diameter of 62.40 mm+/−0.3 mm
UU=radius of 4 mm+/−0.1 mm
VV=1 mm+/−0.1 mm
WW=0.2 mm+/−0.1 mm
XX=radius of 2 mm+/−0.1 mm
YY=radius of 2 mm+/−0.1 mm
ZZ=0.5 mm+/−0.1 mm×45 degrees
AAA=8.50 mm+/−0.2 mm Although the cap 78 has been illustrated as including particular dimensions, the cap 78 may have any other dimensions.

Figure 6:
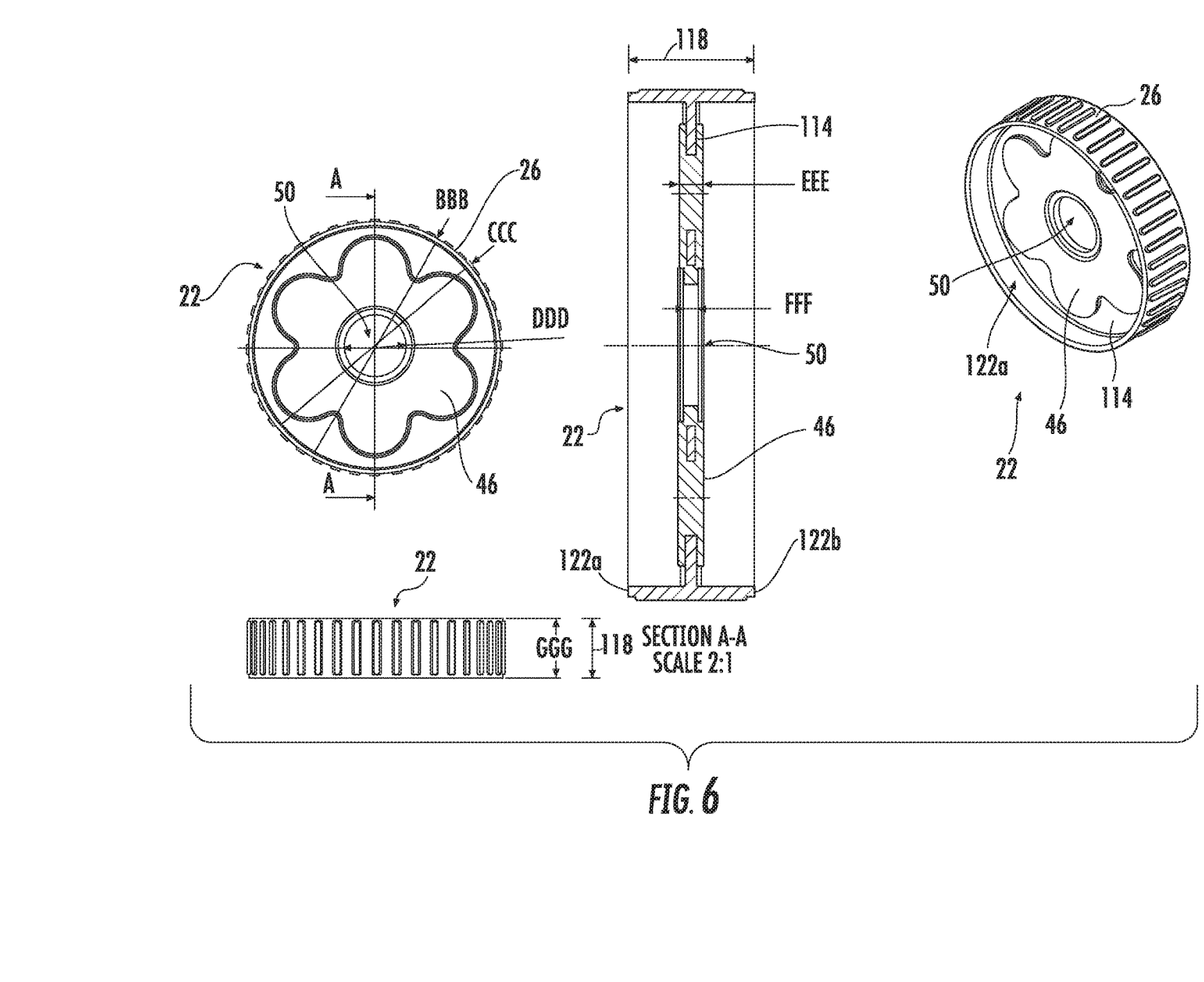
FIG. 6 illustrates another example handle that may be used with a medicinal pen.

FIG. 6 illustrates another example handle 22 that may be used with a medicinal pen 10. As illustrated, the handle 22 includes a frame 26 and a connection surface 46 coupled to the frame 26. In contrast to the handle shown in FIGS. 1A-5 and as further illustrated, the handle 22 of FIG. 6 does not include a cap 78. Instead, in order to inject medicine from the medicinal pen 10, a user may depress the rotary dial 14 by directly contacting the rotary dial 14 with their finger(s) (and/or palm) or directly contacting the rotary dial 14 with another surface, such as a table surface or the surface of a wall, as described further below.

The frame 26 of FIG. 6 may be similar to the frame 26 of FIGS. 1A-5. However, the frame 26 of FIG. 6 may further include a ledge 114 recessed or positioned inside of the depth 118 of the frame 26. The ledge 114 may couple the connection surface 46 to the frame 26. The ledge 114 may have any shape and/or size. Additionally, the ledge 114 may be positioned at any location along the depth 118 of the frame 26. For example, the ledge 114 may be positioned at a location that is equidistant from a first side 122a and a second side 122b of the frame 26, as is illustrated. As another example, the ledge 114 may be positioned at a location that is a different distance from the first side 122a than the second side 122b. In some examples, the distance between the ledge 114 and the first side 122a (and/or second side 122b) may be equal to or approximately equal (i.e., equal +/−1 mm) to half of the height (i.e., the midportion of the height) of the rotary dial 14.

The connection surface 46 of FIG. 6 may be similar to the connection surface 46 of FIGS. A-5. Additionally, the connection surface 46 of FIG. 6 may be coupled to the frame 26 in any of the manners discussed above with regard to connection surface 46 of FIG. 1A-5. As is illustrated, the connection surface 46 is molded with, onto (and/or into) the ledge 114 of the frame 26. When molded with, onto (and/or into) the ledge 114, the connection surface 46 may not be removable from the frame 26 (without, for example, breaking the handle 22). As such, the frame 26 and the connection surface 46 may be a single piece.

As a result of being coupled to the ledge 114, the connection surface 46 may be positioned at the same location along the depth 118 of the frame 26 as the ledge 114. For example, the ledge 114 and the connection surface 46 may both be positioned at a location that is equidistant from a first side 122a and a second side 122b of the frame 26, as is illustrated in FIG. 6. As another example, the ledge 114 and the connection surface 46 may both be positioned at a location that is a different distance from the first side 122a than the second side 122b. For example, the center point of the ledge 114 and the center point of the connection surface 46 may both be positioned at a location that is approximately 4 times (e.g., 4+/−0.5 times) as far from the first side 122a as it is from the second side 122b, approximately 3 times as far from the first side 122a as it is from the second side 122b, approximately 2 times as far from the first side 122a as it is from the second side 122b, approximately 1.5 times as far from the first side 122a as it is from the second side 122b, or any other distance from the first side 122a than the second side 122b.

In some examples, the position of the connection surface 46 along the depth 118 of the frame 26 may be designed to allow the handle 22 to be used with different medicinal pens 10. For example, different medicinal pens 10 may have different heights of the rotary dial 14. In such an example, the position of the connection surface 46 along the depth 118 of the frame 26 may correspond to two different heights of rotary dials 14. That is, the position of the connection surface 46 along the depth 118 of the frame 26 may have a first distance between the connection surface 46 and the first side 122a that is designed to allow a large height rotary dial 14 to be inserted into and grabbed by the connection surface 46, and the position of the connection surface 46 along the depth 118 of the frame 26 may have a second distance between the connection surface 46 and the second side 122b that is designed to allow a small height rotary dial 14 to be inserted into and grabbed by the connection surface 46. In such an example, if the user is using a medicinal pen 10 with a large height rotary dial 14, the handle 22 may be positioned on a surface (such as a table surface) with the first side 122a facing upward so that the large height rotary dial 14 can be inserted into the handle 22. Alternatively, if the user is using a medicinal pen 10 with a small height rotary dial 14, the handle 22 may be flipped around so that the second side 122b is facing upward so that the small height rotary dial 14 can be inserted into the handle 22.

In some examples, the first distance between the connection surface 46 and the first side 122a may be a distance that is equal to or approximately equal (i.e., equal +/−1 mm) to half of the height of the large height rotary dial 14. Additionally, in some examples, the second distance between the connection surface 46 and the second side 122b may be a distance that is equal to or approximately equal (i.e., equal +/−1 mm) to half of the height of the small height rotary dial 14.

As is illustrated, the handle 22 may have the following dimensions:
BBB=diameter of 66.0 mm+/−0.3 mm
CCC=diameter of 67.0 mm+/−0.3 mm
DDD=diameter of 16.0 mm+/−0.2 mm
FEE=3.2 mm+/−0.1 mm
FFF=2.0 mm+/−0.1 mm
GGG=16.0 mm+/−0.3 mm Although the handle 22 has been illustrated as including particular dimensions, the handle 22 may have any other dimensions.

In one example of use of the handle 22 of FIG. 6, the rotary dial 14 may be inserted into the opening 50 of the connection surface 46. The rotary dial 14 may be inserted into the opening 50 of the connection surface 46 in any manner. For example, the user may position the frame 26 onto a surface, such as the surface of a table, and then the user may push the rotary dial 14 into the opening 50 of the connection surface 46. By inserting the rotary dial 14 into the opening 50 of the connection surface 46, the connection surface 46 may grasp the rotary dial 14, as is discussed above. As is also discussed above, the frame 26 may be positioned onto the surface so that either first side 122a or second side 122b is facing upward. In some examples, this positioning may be based on a particular height of the rotary dial 14 of the medicinal pen 10.

When the rotary dial 14 is inserted into the opening 50 of the connection surface 46, a portion of the rotary dial 14 (such as the top portion of the rotary dial 14) may extend through the opening 50 into the other side of the handle 22. For example, if the rotary dial 14 is inserted into the opening 50 through the first side 122a of the handle 22, a portion of the rotary dial 14 may extend through the depth of the opening 50 (and the connection surface 46) into the second side 122b of the handle 22. This may allow the rotary dial 14 to be accessible to a user of the medicinal pen 10 from, for example, the second side 122b of the handle 22. Furthermore, due to this accessibility, the user may be able to touch the top of the rotary dial 14, which may allow the user to depress the rotary dial 14 by directly contacting the rotary dial 14 with their finger(s) (and/or palm) or directly contacting the rotary dial 14 with another surface, such as a table surface or the surface of a wall. As such, a cap 78 may not be needed to depress the rotary dial 14.

Following the insertion of the rotary dial 14 into the opening 50, the frame 26 may be used to select an amount of medicine for injecting into a body of the user. This may be accomplished in any manner, such as rotating the frame 26 so that the rotary dial 14 also rotates.

Following the selection of the amount of medicine to be injected into the body of the user, the injection port 18 of the medicinal pen 10 may be inserted into the body of the user, and the user may depress the rotary dial 14. Because the handle 22 of FIG. 6 does not include a cap 78, the user may depress the rotary dial 14 by directly contacting the rotary dial 14 with their finger(s) (and/or palm) or directly contacting the rotary dial 14 with another surface, such as a table surface or the surface of a wall.

Modifications, additions, combinations, or omissions may be made to the handle 22 of FIGS. 1A-6 without departing from the scope of the disclosure. For example, any of the elements, dimensions, shapes, and/or couplings of the handle 22 of FIGS. 1A-6 may be added to, combined with, or substituted for any of the elements, dimensions, shapes, and/or couplings of the handle 22 of any of the other FIGS. 1A-6. As just one example of this, the handle 22 of FIG. 6 may further include a cap 78.

Figure 7:
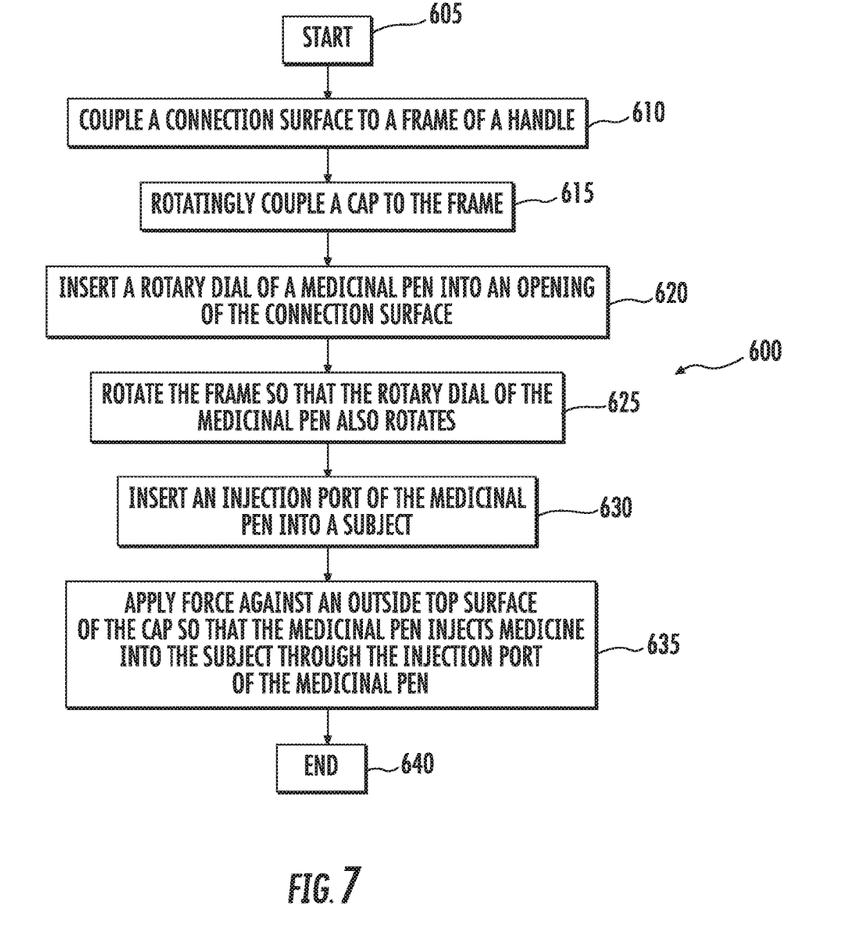
FIG. 7 illustrates an example method of making and/or using a handle.

FIG. 7 illustrates an example method of making and/or using a handle 22. One or more of the steps (such as all of the steps) of method 600 may be performed using the handle 22 (or any of the elements) of FIGS. 1A-6, or any other handle. Furthermore, one or more of the steps (such as all of the steps, for example) of method 600 may be performed by a manufacturer of a handle, a seller of a handle, a re-seller of a handle, and/or a user of a handle.

The method begins at step 605. At step 610, a connection surface may be coupled to a frame of a handle. The connection surface may be any structure that may grasp a rotary dial of a medicinal pen. For example, the connection surface may be connection surface 46 of FIGS. 1A-6. The frame may be any structure that may be used to rotate the rotary dial of the medicinal pen. For example, the frame may be frame 26 of FIGS. 1A-6. The handle may be used with the medicinal pen. In particular, the handle may be inserted onto the rotary dial of the medicinal pen, allowing the handle to be used to assist a user in rotating the rotary dial (e.g., to select an amount of medicine) and to further assist the user in depressing the rotary dial (e.g., to inject the amount of medicine). For example, the handle may be handle 22 of FIGS. 1A-6. The connection surface may be coupled to the frame in any manner, as is discussed above. For example the connection surface may be coupled to the frame using a locking surface, such as locking surface 58 of FIGS. 1A-5.

At step 615, a cap is rotatingly coupled to the frame. The cap may be any structure that may assist the user in depressing (or otherwise pushing down on) the rotary dial of the medicinal pen, and that may further rotate with respect to the frame (and the connection surface). For example, the cap may be cap 78 of FIGS. 1A-5. The cap may be rotatingly coupled to the frame in any manner, as is discussed above. For example, a lip of the cap may be inserted into rotational hooks of the frame. This may couple the cap to the frame, but may allow the cap to rotate with respect to the frame.

At step 620, the rotary dial of the medicinal pen may be inserted into an opening of the connection surface. The medicinal pen may be any pen-like instrument that may be used to inject medicine into a body. For example, the medicinal pen may be medicinal pen 10 of FIGS. 1A-6. The rotary dial of the medicinal pen may be any device that may be rotated in order to select an amount of medicine to be injected using the medicinal pen. Additionally, the rotary dial may further be depressed (or otherwise pushed down on) in order to cause the medicine to be injected. The rotary dial may be rotary dial 14 of FIGS. 1A-6. The rotary dial may be inserted into the opening of the connection surface in any manner. For example, a user may push the rotary dial into the opening of the connection surface. By inserting the rotary dial into the opening of the connection surface, the connection surface may grasp the rotary dial, as is discussed above.

At step 625, the frame may be rotated so that the rotary dial of the medicinal pen also rotates. The frame may be rotated in any manner. As an example, the user may grasp the outer boundary of the frame and twist it, causing the frame to rotate. By rotating the frame (and the connection surface grasping the rotary dial), the rotary dial of the medicinal pen may be rotated. This rotation of the rotary dial may allow the user to select an amount of medicine to be injected.

At step 630, an injection port of the medicinal pen may be inserted into a subject. The injection port may be any port-like device for injecting medicine into a body. For example, the injection port may be injection port 18 of FIGS. 1A-6. The injection port may be inserted into any portion of the body of any type of subject. Furthermore, the injection port may be inserted in any manner.

At step 635, force may be applied against an outside top surface of the cap so that the medicinal pen injects medicine into the subject through the injection port of the medicinal pen. Force may be applied against an outside top surface of the cap in any manner. For example, a user may apply the force using one or more fingers (such as a thumb or index finger), a palm of a hand, one or more hands, a surface (such as pressing the outside top surface of the cap against a desk surface to inject the medicine), any other manner of applying a force, or any combination of the preceding. The force applied by the user may cause one or more protrusions of the cap to focus the force onto the top surface of the rotary dial, which may depress the rotary dial. Furthermore, although the rotary dial may rotate as it is depressed, the rotating coupling of the cap to the frame may cause the cap to not rotate. Instead, only the frame (and the connection surface grasping the rotary dial, and the locking surface) lay rotate. As such, the cap may be easier to press down on. Once the medicine has been injected into the subject, the method 600 may move to step 640, where the method ends.

Modifications, additions, or omissions may be made to method 600. For example, only steps 610-615 may be performed. Alternatively, only steps 620-635 may be performed. As another example, although a handle (such as handle 22) has been discussed above as being used to perform the steps of method 600, in some examples the handle may only be used to perform particular steps. For example, the handle may only be used to rotate the rotary dial of the medicinal pen, as is discussed above with regard to step 625. In such an example, the user may not use the handle to inject the medicine. As another example, the handle may only be used to inject the medicine into the subject, as is discussed above with regard to step 635. In such an example, the user may not use the handle to rotate the rotary dial of the medicinal pen.

This specification has been written with reference to various non-limiting and non-exhaustive embodiments or examples. However, it will be recognized by persons having ordinary skill in the art that various substitutions, modifications, or combinations of any of the disclosed embodiments or examples (or portions thereof) may be made within the scope of this specification. Thus, it is contemplated and understood that this specification supports additional embodiments or examples not expressly set forth in this specification. Such embodiments or examples may be obtained, for example, by combining, modifying, or reorganizing any of the disclosed steps, components, elements, features, aspects, characteristics, limitations, and the like, of the various non-limiting and non-exhaustive embodiments or examples described in this specification. In this manner, Applicant reserves the right to amend the claims during prosecution to add features as variously described in this specification.

What is claimed is:

1. A handle, comprising: a frame having an outer diameter that is between 50 millimeters and 70 millimeters; a connection surface coupled to the frame and configured to grasp a rotary dial of an insulin pen, wherein the connection surface comprises an elastomer washer, wherein the elastomer washer has an opening, configured to receive the rotary dial of the insulin pen, and wherein the opening has an inner diameter that is between 14 millimeters and 17 millimeters; a locking surface coupled to the frame, the locking surface having a first diameter and a second diameter, wherein the second diameter is lamer than the first diameter, and wherein the second diameter of the locking surface is configured to engage one or more locking hooks on the frame to lock the locking surface into the frame, wherein the connection surface is positioned in-between an inside portion of the frame and a bottom portion of the locking surface; a cap rotatingly coupled to the frame, the cap being configured to rotate with respect to the frame, wherein the cap has a protrusion extending from an inside top surface of the cap towards the frame, wherein the protrusion is configured to contact an upper surface of the rotary dial of the insulin pen when a user applies three against an outside top surface of the cap; and wherein the frame and connection surface are configured to be rotated with respect to the cap by a rotation of the rotary dial of the insulin pen.

2. The handle of claim 1, wherein the inner diameter is approximately 1 millimeter smaller than an outer diameter of the rotary dial of the insulin pen.

3. The handle of claim 1, wherein the cap has an outer diameter that is between 49 millimeters and 70 millimeters.

4. The handle of claim 1, wherein the cap has one or more rubber tips positioned on an outside top surface of the cap.

5. A method, comprising: coupling a connection surface to a frame of a handle, the frame having an outer diameter that is between 50 millimeters and 70 millimeters, the connection surface being configured to grasp a rotary dial of a medicinal an insulin pen, wherein the connection surface comprises an elastomer washer, wherein the elastomer washer has an opening configured to receive the rotary dial of the insulin pen, and wherein the opening has an inner diameter that is between 14 millimeters and 17 millimeters; coupling a locking surface to the frame, the locking surface having a first diameter and a second diameter, wherein the second diameter is larger than the first diameter, and wherein the second diameter of the locking surface is configured to engage one or more locking hooks on the frame to lock the locking surface into the frame, wherein the connection surface is positioned in-between an inside portion of the frame and a bottom portion of the locking surface; rotatingly coupling a cap to the frame, the cap being configured to rotate with respect to the frame, wherein the cap has a protrusion extending from an inside top surface of the cap towards the frame, wherein the protrusion is configured to contact an upper surface of the rotary dial of the insulin pen when a user applies force against an outside top surface of the cap; and wherein the frame and connection surface are configured to be rotated with respect to the cap by a rotation of the rotary dial of the insulin pen.

6. The method of claim 5, wherein the inner diameter is approximately 1 millimeter smaller than an outer diameter of the rotary dial of the insulin pen.

7. The method of claim 5, further comprising:
inserting the rotary dial of the insulin pen into the opening of the connection surface so that the connection surface grasps the rotary dial of the insulin pen;
rotating the frame so that the rotary dial of the insulin pen also rotates;
inserting an injection port of the insulin pen into a subject; and
applying force against an outside top surface of the cap so that the insulin pen injects insulin into the subject through the injection port of the insulin pen.

* * * * *